United States Patent
Biedermann et al.

(10) Patent No.: US 12,383,312 B2
(45) Date of Patent: Aug. 12, 2025

(54) COUPLING DEVICE FOR COUPLING A ROD TO A BONE ANCHOR AND SYSTEM INCLUDING SUCH A COUPLING DEVICE AND AT LEAST TWO BONE ANCHORS

(71) Applicant: BIEDERMANN TECHNOLOGIES GMBH & CO. KG, Donaueschingen (DE)

(72) Inventors: Lutz Biedermann, VS-Villingen (DE); Timo Biedermann, Trossingen (DE); Bernd Fischer, Friedenweiler (DE); Berthold Dannecker, St. Georgen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 0 days.

(21) Appl. No.: 18/981,083

(22) Filed: Dec. 13, 2024

(65) Prior Publication Data

US 2025/0195111 A1 Jun. 19, 2025

Related U.S. Application Data

(60) Provisional application No. 63/610,832, filed on Dec. 15, 2023.

(30) Foreign Application Priority Data

Dec. 15, 2023 (EP) ..................................... 23217301

(51) Int. Cl.
*A61B 17/70* (2006.01)
*A61B 17/00* (2006.01)

(52) U.S. Cl.
CPC ................... *A61B 17/7038* (2013.01); *A61B 2017/00477* (2013.01)

(58) Field of Classification Search
CPC .................. A61B 17/7038; A61B 2017/00477
See application file for complete search history.

(56) References Cited

U.S. PATENT DOCUMENTS 7,749,258 B2 7/2010 Biedermann et al.
8,192,470 B2 * 6/2012 Biedermann ...... A61B 17/7037
606/267

(Continued)

FOREIGN PATENT DOCUMENTS

EP 3 673 844 A1 7/2020
EP 3 878 386 A1 9/2021

(Continued)

OTHER PUBLICATIONS

Extended European Search Report for Application No. 23217301.3, mailed Jun. 7, 2024, 11 pages.

(Continued)

*Primary Examiner* — Sameh R Boles
(74) *Attorney, Agent, or Firm* — Womble Bond Dickinson (US) LLP

(57) ABSTRACT

A system for coupling a rod to bone includes different first and second bone anchors and a coupling device including a receiving part with a rod receiving portion for receiving a rod and a head receiving portion for interchangeably accommodating a head of either the first or second bone anchors, and a locking member positionable at least partially around the head receiving portion and movable between a first position where the held head is movable relative to the receiving part and a second position where the held head is locked relative to the receiving part. The coupling device includes a restraining surface configured to restrict pivoting of the first bone anchor relative to the receiving part, while the coupling device is configured to restrict pivoting of the second bone anchor relative to the receiving part differently (Continued)

than the restricted pivoting of the first bone anchor relative to the receiving part.

20 Claims, 9 Drawing Sheets

(56) References Cited

U.S. PATENT DOCUMENTS

| | | |
|---|---|---|
| 8,888,827 B2 | 11/2014 | Harper et al. |
| 9,277,938 B2 | 3/2016 | Biedermann et al. |
| 2007/0090238 A1 | 4/2007 | Justis |
| 2010/0324599 A1 | 12/2010 | Montello et al. |
| 2012/0046701 A1 | 2/2012 | Gennari et al. |
| 2016/0113684 A1 | 4/2016 | Rezach et al. |
| 2017/0143379 A1 | 5/2017 | Walker et al. |
| 2019/0046242 A1 | 2/2019 | Vedula et al. |
| 2019/0105085 A1 | 4/2019 | Hawkes et al. |
| 2021/0059723 A1 | 3/2021 | Biedermann et al. |
| 2022/0087721 A1 | 3/2022 | Yacoub |
| 2023/0008092 A1 | 1/2023 | Jackson et al. |
| 2023/0270469 A1 | 8/2023 | Biedermann et al. |

FOREIGN PATENT DOCUMENTS

| | | |
|---|---|---|
| EP | 4 074 271 A1 | 10/2022 |
| WO | WO 2014/169189 A1 | 10/2014 |

OTHER PUBLICATIONS

Extended European Search Report for Application No. 23165563.0, mailed Sep. 27, 2023, 9 pages.

* cited by examiner

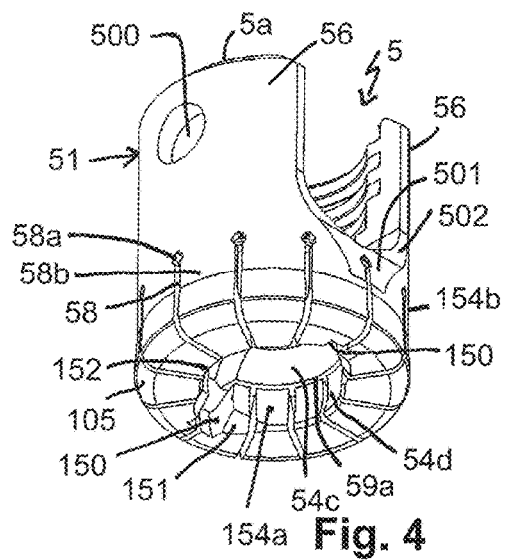
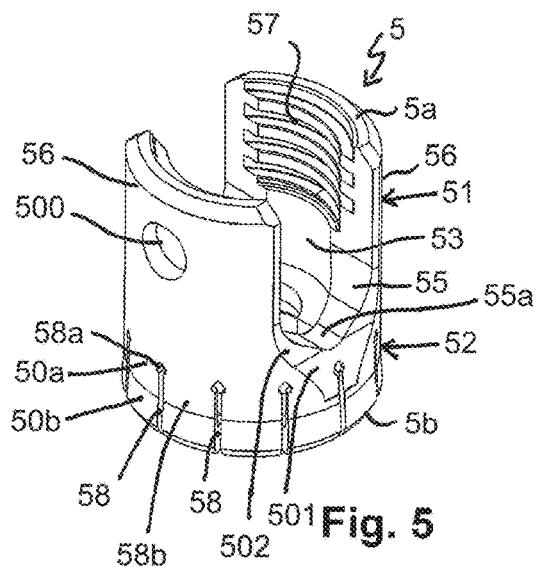
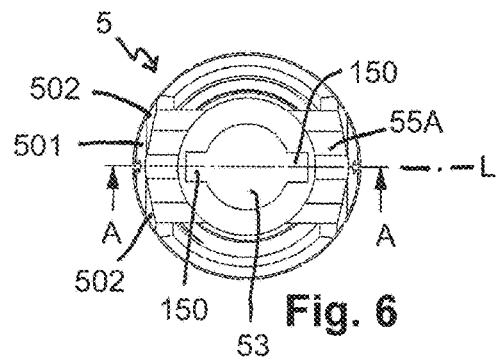
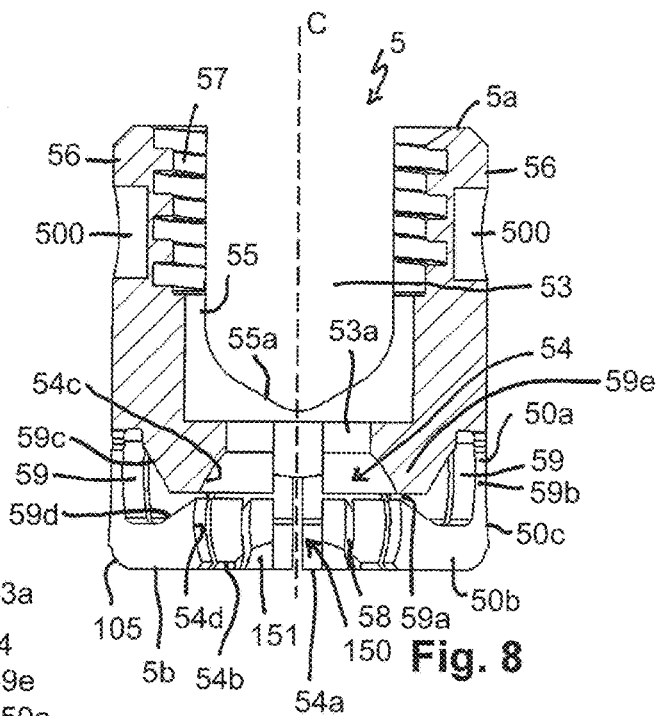
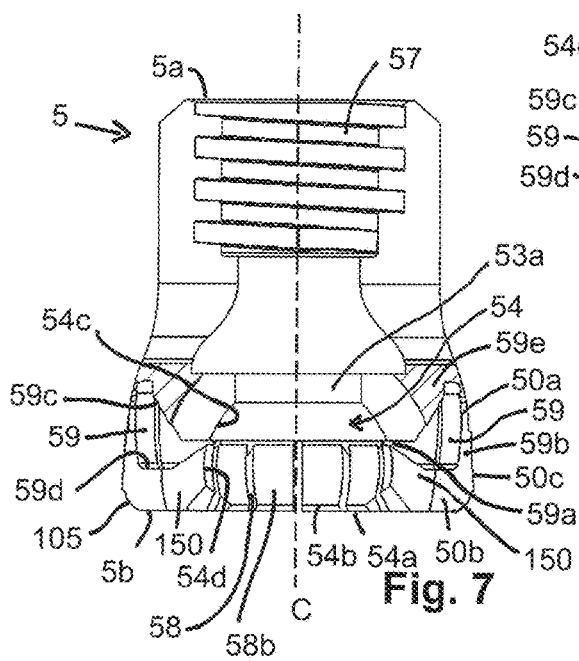

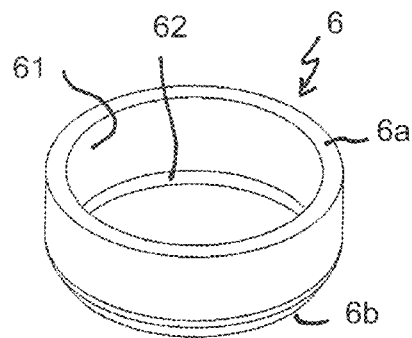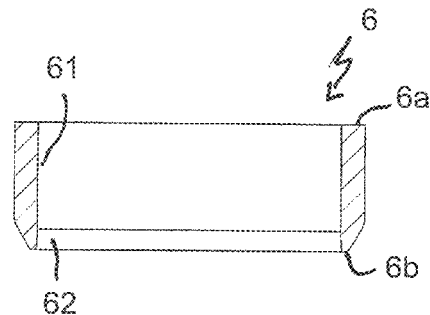
Fig. 9
Fig. 10
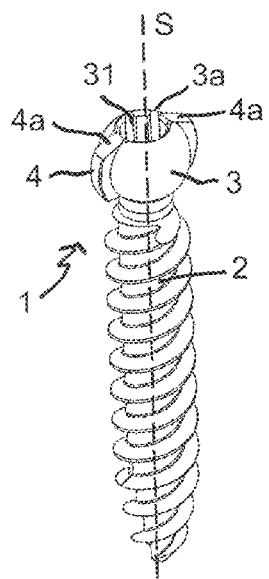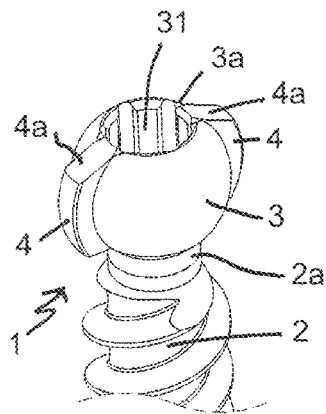
Fig. 11
Fig. 12
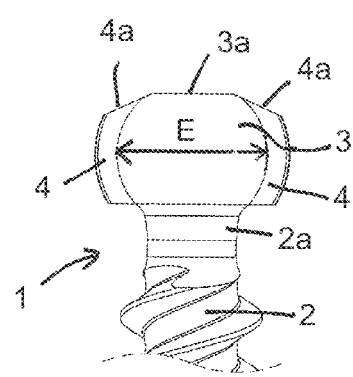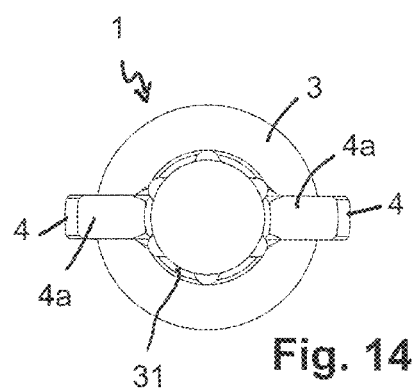
Fig. 13
Fig. 14

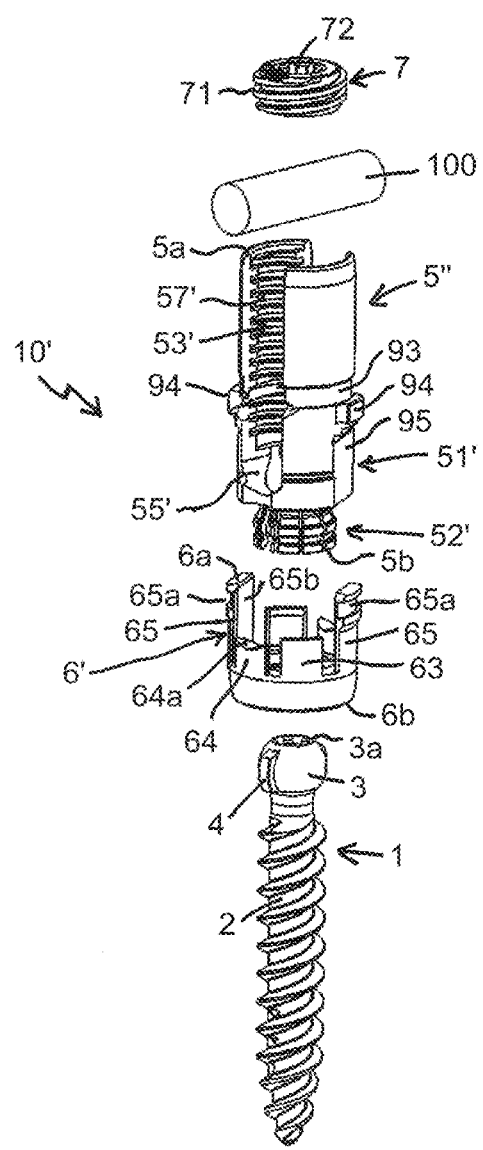
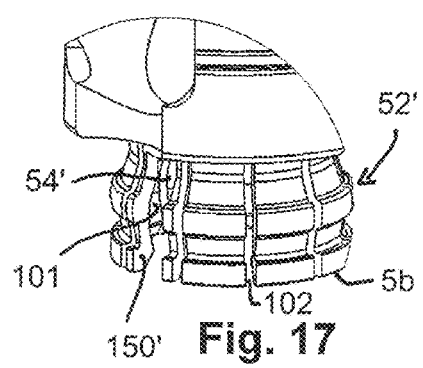
Fig. 16
Fig. 17

COUPLING DEVICE FOR COUPLING A ROD TO A BONE ANCHOR AND SYSTEM INCLUDING SUCH A COUPLING DEVICE AND AT LEAST TWO BONE ANCHORS

CROSS-REFERENCE TO RELATED APPLICATION(S)

The present application claims priority to and the benefit of U.S. Provisional Patent Application No. 63/610,832, filed Dec. 15, 2023, the contents of which are hereby incorporated by reference in their entirety, and claims priority from European Patent Application EP 23 217 301.3, filed Dec. 15, 2023, the contents of which are hereby incorporated by reference in their entirety.

BACKGROUND

Field

The present application relates to a coupling device for coupling a rod to a bone anchor, to a bone anchoring device including such a coupling device, and to a bone anchoring system including such a coupling device and at least two bone anchors.

Description of Related Art

Coupling devices are used in orthopedic surgery, in particular in spinal surgery, for coupling a rod to a head of a bone anchor that is anchored in bone or in a vertebra. The head of the bone anchor may be pivotably received in a receiving part of the coupling device which also accommodates the rod, so that the receiving part can assume various angular positions with respect to the bone anchor. Thus, a suitable orientation of the bone anchor with respect to the rod can be achieved.

In order to lock an inserted head at a specific angular position with respect to the receiving part, EP 4 074 271 A1 describes a receiving part with a head receiving portion for accommodating a head of an anchoring element, and a locking member that is mountable to the receiving part such that it embraces the head receiving portion. The locking member is designed as an outer ring, and is movable between a first position and a second position. In the second position, the locking member compresses the head receiving portion to lock the inserted head. In addition, the head receiving portion has a locally reduced wall thickness to facilitate spreading of the head receiving portion to easily insert the head of the bone anchor, whereas a thicker wall portion of the head receiving portion provides for sufficient strength and stability when clamping the inserted head.

The bone anchoring device described in EP 4 074 271 A1 is a polyaxial bone anchoring device configured such that a bone anchor can pivot with respect to a receiving part in multiple planes. Depending on the use or clinical application, it can be desirable to provide a bone anchoring device configured to restrict pivoting of the bone anchor with respect to the receiving part to a single plane, i.e., a monoplanar bone anchoring device, or a monoaxial bone anchoring device configured to prevent pivoting of the bone anchor with respect to the receiving part.

Various designs of monoplanar bone anchoring devices are known where the shank of a bone anchor can pivot in the receiving part only in a single plane. For example, U.S. Pat. No. 7,749,258 B2 describes a monoplanar bone anchoring device including a receiving part for receiving a rod, a pressure element, and a bone anchoring element being movable relative to the receiving part in a limited angular range about the longitudinal axis of the receiving part, the angles lying in a single plane. The movement of the bone anchoring element relative to the receiving part is limited by a form fit connection including cooperating guiding surfaces at the head of the bone anchoring element and at the pressure element.

SUMMARY

There is still a need to provide a coupling device having a simple structure with only few parts, that may facilitate implementation of at least a polyaxial and/or a monoplanar bone anchoring device.

Thus, it is an object underlying the invention to provide a coupling device that can be used in a modular bone anchoring device, that enables a selectable functionality in terms of a polyaxial and a monoplanar design. It is also an object to provide a bone anchoring system that includes such a coupling device and at least two bone anchors that provide different functionality to the bone anchoring device.

According to an embodiment of the invention, a coupling device for selectively coupling a rod to a first bone anchor of a first type or to a second bone anchor of a second type is provided. The coupling device includes a receiving part having a first end, an opposite second end, and a central axis extending through the first end and the second end, the receiving part including a rod receiving portion for receiving the rod, and a head receiving portion having an accommodation space for pivotably receiving a head of the first bone anchor or a head of the second bone anchor, such that a shank of the first bone anchor or a shank of the second bone anchor can assume a plurality of angular positions relative to the central axis. The coupling device further includes a locking member positionable at least partially around the head receiving portion and movable between at least a first position where the head is pivotable and a second position where the head is locked in the accommodation space. The head receiving portion includes a restraining structure, by means of which the coupling device is configured to cooperate with the first bone anchor such that the first bone anchor is configured to pivot with respect to the central axis in a single plane, or with the second bone anchor such that the second bone anchor is configured to pivot with respect to the pivot axis in multiple planes, when the locking member is in the first position.

By selecting and assembling the first bone anchor with the coupling device, the coupling device can be used as a monoplanar bone anchoring device. By selecting and assembling the second bone anchor with the coupling device, the coupling device can be used as a polyaxial bone anchoring device. Since the same coupling device can be used with different bone anchors, the surgeon has a more flexible and versatile choice of implant combinations, while the number of parts per set is reduced.

Thus, with a coupling device according to embodiments of the invention, a modular bone anchoring device can be implemented that can, at the choice of the user, be assembled from few interchangeable parts to allow for uses for different applications.

A bone anchoring device with a coupling device according to embodiments of the invention, as described above, may be of a bottom loading type, i.e., the bone anchor can be inserted from a bottom end of the coupling device. This enables assembly either prior to surgery, or during surgery in situ when the bone anchor is already inserted into bone.

In addition, since the coupling device may be more expensive and/or difficult to manufacture compared to the bone anchor, the manufacturing costs and/or the costs for stockholding can be decreased if the same coupling device can be used with various different bone anchors for more than one clinical application.

For example, the coupling device or three-dimensional parts thereof may be manufactured using an additive manufacturing method, such as printing, for example laser sintering or laser or electron beam melting. With such a method complex shapes can be easily manufactured on the basis of CAD data of the object to be manufactured.

According to a further embodiment, a receiving part is provided that has a first end, an opposite second end, and a central axis extending through the first end and the second end. The receiving part includes a rod receiving portion for receiving the rod and a head receiving portion that defines an accommodation space for receiving a head of a bone anchor. The head receiving portion further has a number of slits that are open to the second end of the receiving part, the slits forming a number of wall sections of the head receiving portion. The slits and wall sections preferably render the head receiving portion flexible, in particular compressible and/or expandable. Further, at least one cutout portion is provided at the head receiving portion by removing, preferably cutting away, at least a portion of one or more of the wall sections. Preferably, the cutout portion is configured to receive at least a portion of a shank of the bone anchor therein to provide for an enlarged pivot angle of the bone anchor in a predefined direction with respect to the central axis, or at least a limited angular range in a circumferential direction of the receiving part.

As used in the present specification and the appended claims, the term "rod" shall be understood as including any elongate member, regardless of the cross-sectional shape of the elongate member. Specifically, a spinal stabilization rod as used herein may have a substantially circular, oval, or angular cross-section. Such a cross-section may further vary along a length of the rod.

BRIEF DESCRIPTION OF THE DRAWINGS

Further features and advantages will become apparent from the description of embodiments by means of the accompanying drawings. In the drawings:

FIG. 4 shows a perspective view from a bottom of a receiving part of the coupling device shown in FIGS. 1 to 3.

FIG. 5 shows a perspective view from a top of the receiving part of FIG. 4.

FIG. 6 shows a top view of the receiving part of FIGS. 4 and 5.

FIG. 7 shows a cross-sectional view of the receiving part of FIGS. 4 to 6, the cross-section taken along line A-A in FIG. 6.

FIG. 8 shows a cross-sectional view of the receiving part of FIGS. 4 to 7, the cross-section taken perpendicular to the line A-A in FIG. 6.

FIG. 9 shows a perspective view from a top of a locking member of the coupling device shown in FIGS. 1 to 3.

FIG. 10 shows a cross-sectional view of the locking member of FIG. 9, the cross-section taken perpendicular to a central axis of the locking member.

FIG. 11 shows a perspective view of an embodiment of a first bone anchor of the system of FIG. 1.

FIG. 12 shows a perspective view of a portion of the first bone anchor of FIG. 11.

FIG. 13 shows a side view of a portion of the first bone anchor of FIGS. 11 and 12.

FIG. 14 shows a top view of the first bone anchor of FIGS. 11 to 13.

FIG. 16 shows a perspective exploded view of a bone anchoring device including a coupling device according to a further embodiment and a bone anchor.

FIG. 17 shows an enlarged perspective view of a lower part of a receiving part of the bone anchoring device of FIG. 16.

DETAILED DESCRIPTION

Figure 1:
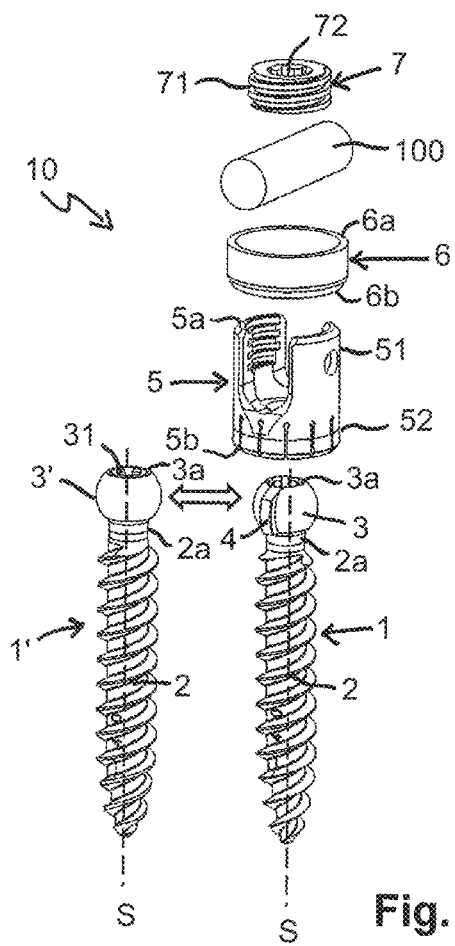
FIG. 1 shows a perspective exploded view of a system according to an embodiment of the invention, including a coupling device and two bone anchors that can be used in an interchangeable manner with the coupling device.

Referring to FIG. 1, a system including a coupling device and two bone anchors according to an embodiment of the invention includes a first bone anchor 1 of a first type, a second bone anchor 1' of a second type, and a coupling device 10 that is interchangeably connectable to the first bone anchor 1 or the second bone anchor 1'. When the coupling device 10 is assembled with the first bone anchor 1, the resulting bone anchoring device is an monoplanar bone anchoring device in which the first bone anchor 1 can pivot only in a single plane relative to the coupling device. When the coupling device is assembled with the second bone anchor 1', the resulting bone anchoring device is a polyaxial bone anchoring device in which the bone anchor 1' can pivot in multiple planes relative to the coupling device. Thus, the first bone anchor 1 and the second bone anchor 1' may be interchangeably used together with one and the same coupling device 10.

The coupling device 10 includes a receiving part 5 and a locking member 6. The receiving part 5 includes a rod receiving portion 51 for receiving a rod 100, and a head receiving portion 52 for accommodating a head 3 of the first bone anchor 1 or a head 3' of the second bone anchor 1'. Preferably, the receiving part is a monolithic piece. The locking member 6 is positionable around the head receiving portion 52 of the receiving part 5 and is movable between at least a first position and a second position along an outer surface of the receiving part 5. The locking member 6 is configured to exert pressure onto the head receiving portion 52 and onto an inserted head at least when the locking member 6 is in the second position to lock the head in the receiving part 5 at a particular angular position relative to the shank 2. Preferably, the locking member 6 is a closed ring.

Figure 2:
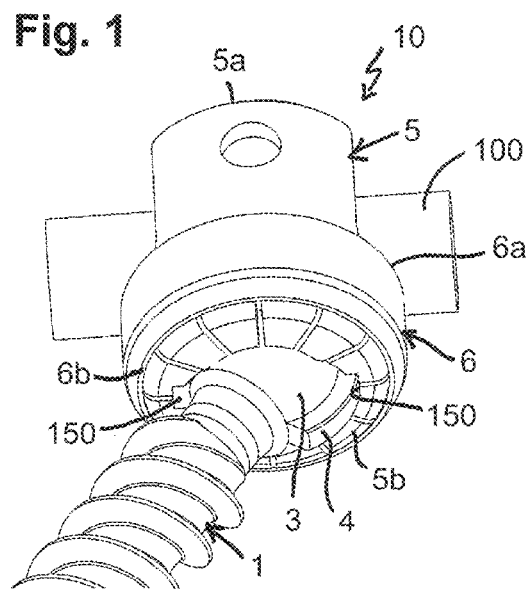
FIG. 2 shows a perspective view of an embodiment of a bone anchoring device with parts of the system of FIG. 1 in an assembled state.
Figure 3:
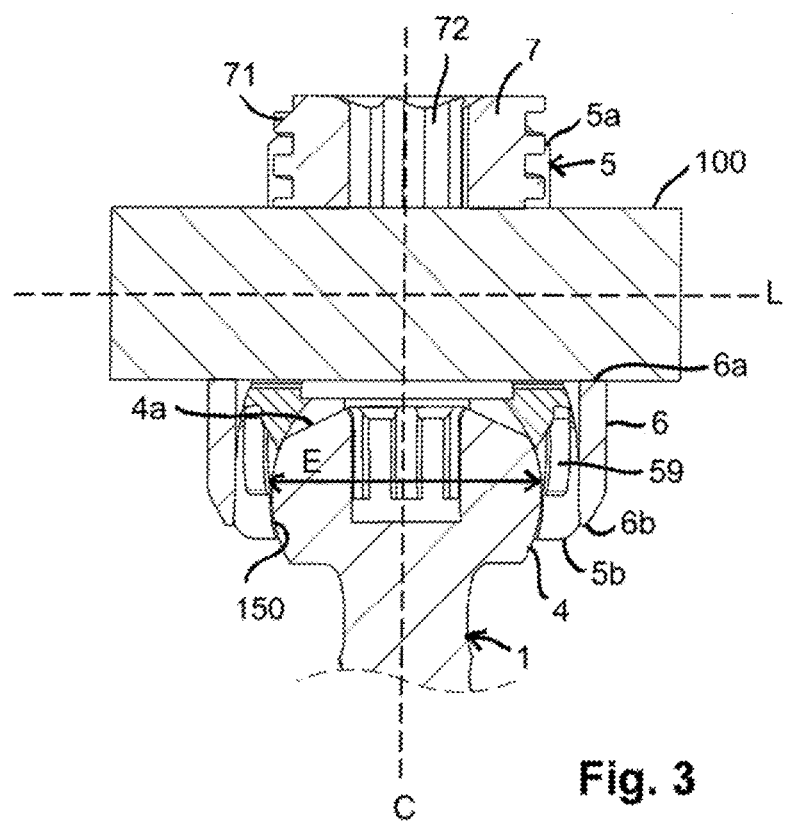
FIG. 3 shows a cross-sectional view of the bone anchoring device of FIG. 2, the cross-section taken in a plane including a central axis of the receiving part and a longitudinal axis of an inserted rod.

The coupling device 10 further includes a fixation member in the form of, for example, a fixation screw 7 for securing and fixing the rod 100 in the receiving part 5. The fixation member 7 includes an engagement structure at an outer surface thereof, for example, an external thread 71, and a tool engagement recess 72. The fixation member 7 may be, for example, a set screw that can be screwed into the receiving part 5. FIGS. 2 and 3 show the first bone anchor 1 assembled with the coupling device 10 and the rod 100 inserted and fixed by the fixation member 7.

As depicted in greater detail in FIGS. 4 to 8, the receiving part 5 may be substantially cylindrical and has a first end or top end 5a, a second end or bottom end 5b, and a passage or bore 53 extending from the first end 5a towards the second end 5b and defining a longitudinal central axis C extending through the first end 5a and the second end 5b. The rod receiving portion 51 is formed adjacent the first end 5a and the head receiving portion 52 is formed at the second end 5b.

The passage 53 extends from the first end 5a to a distance therefrom and merges into an intermediate portion 53a that has a reduced diameter. The intermediate portion 53a may be, for example, cylindrical. Adjacent to the intermediate portion 53a, an accommodation space 54 is formed that is shaped and sized to accommodate the head 3 of the first bone anchor 1 or the head 3' of the second bone anchor 1' therein. The accommodation space 54 has an opening 54a at the second end 5b of the receiving part 5.

A substantially U-shaped recess 55 extends from the first end 5a of the receiving part 5 to a distance therefrom. The substantially U-shaped recess 55 divides the receiving part 5 into two legs 56 and forms a channel with a longitudinal axis L for receiving the rod 100. A bottom 55a of the channel may have a substantially V-shaped upper contour, which provides a rod support surface for an inserted rod 100. By means of this, rods with different diameters may be inserted into the channel and can be more stably supported on the rod support surface. An internal thread 57, for example a flat thread or a square thread, is formed in the passage 53 on the legs 56 adjacent to the first end 5a for cooperating with the external thread 71 of the fixation member 7. By means of the U-shaped recess 55, the upper portion of the receiving part defines the rod receiving portion 51.

A lower portion of the receiving part 5, which may extend approximately from the intermediate portion 53a of the passage 53 to the second end 5b, which includes the accommodation space 54, defines the head receiving portion 52 of the receiving part 5. The accommodation space 54 has a substantially spherical inner contour that matches an outer contour of the head 3 of the first bone anchor 1 and an outer contour of the head 3' of the second bone anchor 1'. The axial extension of the accommodation space 54 in the direction of the central axis C is such that the accommodation space is configured to cover a region of the spherical portion of the head 3 or 3' with a greatest outer diameter E of the selected head when the head is inserted into the accommodation space 54. More specifically, the size of the accommodation space 54 may be such that the head 3 of the first bone anchor 1 or the head 3' of the second bone anchor 1' can be held therein by friction. A small chamfered portion 54b may be provided for facilitating the insertion of the head. As can be seen in particular in FIGS. 7 and 8, the accommodation space 54 is divided into an upper portion 54c configured to cover the head 3, 3' from the top and a lower portion including a seat 54d for the head 3, 3', in which the head can pivot.

A wall of the receiving part 5 around the accommodation space 54 is expandable and compressible in a radial direction with respect to the central axis C. This may be achieved by a plurality of axially extending slits 58 that are open to the second end 5b and that may extend up to a distance from the second end 5b, preferably up to the intermediate portion 53a of the passage 53. An end portion 58a of the slits 58 is enlarged, for example, with a diamond-shaped contour, a circular contour, or a triangular contour, or any other suitable shape. The slits 58 form a number of flexible wall sections 58b of the head receiving portion 52. The size and number of the slits 58 may be selected such as to obtain a desired flexibility of the head receiving portion 52.

A cavity 59 is formed in the wall of the head receiving portion 52, the cavity 59 extending circumferentially around the accommodation space 54. The cavity 59 may extend in the axial direction of the central axis C from a position below a region accommodating the greatest diameter E of the head up to the end portions 58a of the slits 58. Thus, the cavity 59 encircles an inserted head circumferentially and extends along a substantial region in the direction of the central axis C along or around the head 3, 3'. Moreover, the cavity 59 is in communication with the accommodation space 54 through an opening 59a, which has a smaller width in the direction of the central axis C than a radially outer portion of the cavity 59. More specifically, the opening 59a has the shape of an annular slit, as can be seen in particular in FIGS. 4, 7, and 8. An outwardly directed wall portion 59b defining the cavity 59 may be such that a shape of the cavity 59 at the wall portion 59b is slightly convex, and the wall portion 59b may be formed at a radial position away from the central axis C so that a radially outermost wall portion 50a of the head receiving portion 52 is thinner than a lowermost wall portion 50b below the cavity 59 at or adjacent to the second end 5b. Also, the end portions 58a of the slits 58 are in communication with the cavity 59. A virtual connection line between two adjacent end portions 58a of the slits 58 may thus, together with the radially thinner wall portion 50a of the head receiving portion 52, define a predetermined breaking point or breaking line for removing a portion of the respective wall section 58b, as explained in more detail below.

An upper wall portion 59c of the wall defining the cavity 59 may be inclined and tapered to narrow towards the central axis C as the upper wall portion 59c extends towards the second end 5b up to the opening 59a. A lower wall portion 59d of the wall defining the cavity 59 may be substantially flat in a direction substantially perpendicular to the central axis C and may then rise in a curved or inclined manner towards the opening 59a. It shall be noted that the detailed shape of the cavity is not limited to the embodiment shown, but may vary.

By the opening 59a of the cavity 59, the accommodation space 54 is divided into the upper portion 54c and the seat 54d, the latter of which can be pressed against the head 3, 3' by the locking member 6. The upper portion 54c of the accommodation space is at least partially delimited by an interior wall portion 59e located above the opening 59a.

The wall portion 50a is thin compared to the wall portion 50b when measured in the radial direction. Due to the cavity 59, the flexible wall sections 58b of the wall portion 50b can be easily spread, even though they are relatively thick at the second end 5b of the receiving part 5. When the head receiving portion 52 is compressed by the locking member 6, as described below, the lowermost wall portion 50b is configured to exert pressure onto the head 3, 3' from an axial position at or close to the region with the greatest diameter E of the head and from below this region, as depicted in FIG. 3. Since the wall sections 58b of the wall portion 50b are thicker closer to the second end 5b, a sufficiently strong clamping force can be achieved. Also, the strength against loosening may be enhanced by this design. In other words, the wall sections provide a stable seat 54d for the head 3, 3', in which the inserted head can be safely clamped.

The outer surface of the wall of the head receiving portion 52 widens towards the second end 5b in a tapered portion 50c close to the second end 5b. Thereby, the compression force increases when the locking member 6 is moved along the head receiving portion 52 in a direction towards the second end 5b or away from the first end 5a. Between the tapered portion 50c and the second end 5b, an outer surface portion 105 may be convexly rounded.

As best shown in FIGS. 4 and 6 to 8, two opposite recesses or slots 150 are formed at the bottom end 5b of the head receiving portion 52. The recesses 150 are offset from each other by 180° and are aligned with the longitudinal axis L defined by the channel when seen in a top view, as shown in FIG. 6. In greater detail, the recesses 150 extend from the bottom end 5b through the seat 54d and the upper portion 54c of the accommodation space 54 up to the intermediate portion 53a. An inner contour of the recesses 150 may be substantially rectangular. The recesses 150 may be provided at circumferential positions of the receiving part 5 where slits 58 are formed, i.e., the recesses 150 may include or house a slit 58, for example, as shown in FIG. 4. In the radial direction, the recesses 150 extend from an inner surface 154a of the wall of the head receiving portion 52 towards an outer surface 154b of the wall, and end at a distance from the outer surface 154b, as shown in FIG. 4. Hence, the recesses 150 are open towards the accommodation space 54, but do not extend entirely through the wall of the receiving part 5 in the radial direction. Moreover, the recesses 150 do not substantially extend into the cavity 59.

By means of the recesses 150, it is possible to insert the head 3 of the first bone anchor 1 from the bottom end 5b, as explained further below. Specifically, the recesses 150 define a restraining structure or a part of such a restraining structure, that restrains a pivoting or rotational motion of an inserted head 3 of the bone anchor 1 of the first type relative to the receiving part to a single plane including the central axis C.

The receiving part 5 further has cutaway portions 151 formed adjacent to both sides of one of the recesses 150 which are configured to receive a portion of the shank 2 of the bone anchor therein. The cutaway portions 151 are formed in an inner edge 152 around the lower opening 54a of the receiving part 5. An axial and radial extension of the cutaway portions 151 is smaller than an axial and radial extension of the recess 150. The cutaway portions 151 may have a substantially triangular shape and form chamfered surfaces that gradually merge from the edge 152 into the recess 150. Thus, the cutaway portions 151 provide for an enlarged pivot angle that the shank axis S of the first bone anchor 1 or of the second bone anchor 1' can form with the central axis C when pivoting to the position of the cutaway portions 151. It shall be noted that the cutaway portions 151 may be formed at both sides of each of the recesses 150.

At the center of each leg 56 in a circumferential direction, a through hole 500 or another engagement structure may be provided for engagement with an instrument. Moreover, inclined cutaway portions 501 may be formed at either end of the channel for the rod, close to the bottom 55a of the substantially U-shaped recess. Additional chamfered portions 502 may extend from the cutaway portions 501 to some extent towards the edges of each of the legs 56 on either side of the channel. The cutaway portions 501 and chamfered portions 502 may facilitate the mounting of the locking member 6 from the first end 5a of the receiving part 5 and/or reduce the size of the receiving part 5.

Referring additionally to FIGS. 9 and 10, the locking member 6 will be described in greater detail. The locking member 6 is formed as a closed ring, with a first or upper end 6a and a second or lower end 6b. An inner surface 61 of the locking member 6 is substantially cylindrical with an inner diameter sized such that the locking member 6 fits around the receiving part 5 and is configured to slide along the outer surface of the receiving part 5. Adjacent to the second end 6b, the locking member 6 may include a tapered inner surface portion 62 that tapers and narrows towards the first end 6a, and is configured to cooperate with the tapered outer surface portion 50c of the receiving part 5. The angle of the tapered portions of the locking member 6 and the receiving part 5 preferably correspond to each other. Preferably, the angle is selected such that a self-locking occurs when the surfaces engage each other. Thus, once the locking member 6 is mounted and the tapered surfaces engage each other, the locking member 6 is prevented from being inadvertently moved upward and loosening the locking mechanism. However, it may be possible to disengage the cooperating surfaces, for example, by using an instrument.

The outer surface of the locking member 6 may be cylindrical and may include an engagement structure for engagement with an instrument (not shown in the figures). Adjacent to the second end 6b, the outer surface may be tapered and narrow towards the second end 6b. However, the shape is not limited to such a design. The axial length of the locking member 6 between the first end 6a and the second end 6b may be at least the axial extension of the cavity 59 of the receiving part 5, preferably greater than the axial length or height of the cavity 59. Thus, the locking member 6 is configured to exert a radial compression force onto a major part of the head receiving portion 52 of the receiving part. The locking member 6 can be mounted to the receiving part 5 from the second end 5b of the receiving part 5 or from the first end 5a thereof.

Referring further to FIGS. 11 to 14, the first bone anchor 1 will be described in greater detail. The bone anchor 1 includes a shank 2 with a shank axis S, wherein the shank is preferably fully or partially threaded, and a head 3 with a free end 3a. Between the head 3 and the shank 2, there may be a neck portion 2a. The head 3 has a spherical outer surface portion that includes a region with the greatest diameter E of the sphere. Preferably, the spherical outer surface portion may be, in the axial direction, substantially symmetrical with respect to a plane including the plane of the greatest outer diameter E. In addition, the head 3 includes two opposite wings 4 that project from the spherical surface of the head away from the shank axis S. Each wing 4 extends parallel to the shank axis S along the spherical surface of the head 3. The wings may extend from the free end 3a of the head 3 up to the neck 2a, or may be provided at a distance from the free end 3a of the head and/or at a distance from the neck 2a.

The wings 4 are offset by 180° along the circumferential direction of the head 3, and may be symmetrical with respect to a middle plane including the shank axis S. Each wing 4 has a shape of a spherical shell segment. An upper end 4a of the wings 4 may be flat and slightly inclined to widen towards the shank 2. However, the upper end 4a may also be curved. A width of the wings 4 is such that when the head 3 is received in the head receiving portion 52 of the receiving part 5, the wings 4 can extend into the recesses 150 and pivot therein. Thus, the wings 4 form a restraining structure or a part of a restraining structure that cooperates with a corresponding restraining structure in the form of the recesses 150 provided at the receiving part 5, to limit or restrain the pivoting motion of the head 3 in the accommodation space 54 to a single plane. It shall be noted that the width of the wings 4 is such that when the head 3 passes through the lower opening 54a of the receiving part 5 during insertion, the wings 4 pass through the recesses 150 at the bottom end 5b of the receiving part 5.

Moreover, at the free end 3a of the bone anchor 1, a tool engagement recess 31 is formed that may have a polygonal or any other shaped engagement structure such as, for example, a torx-shaped or star-shaped or other axial groove-shaped structure suitable to screw the bone anchor 1 into bone.

Referring to FIG. 1, the second bone anchor 1' will be described in greater detail. Parts and portions of the second bone anchor 1' that are identical to the first bone anchor 1 are marked with the same or similar reference numerals, and the descriptions thereof will not be repeated. The second bone anchor 1' differs from the first bone anchor 1 in that the head 3' of the second bone anchor lacks the wings 4. Hence, the outer surface of the head 3' is uniformly spherically-shaped between the neck portion 2a and the free end surface 3a. As a result, when the second bone anchor 1' is inserted into the coupling device 10, the head 3' can freely pivot in the accommodation space 54 of the receiving part 5 without the angular motion between the respective parts being restrained to a single plane. This means the second bone anchor 1' can pivot relative to the central axis C in multiple planes, even in an unlimited number of planes.

Parts and portions of the polyaxial bone anchoring device may be made of any material, preferably, however, of a bio-compatible material, such as titanium or stainless steel, or any other bio-compatible metal or metal alloy, or plastic material. For a bio-compatible alloy, a NiTi-alloy, for example Nitinol, may be used. Other materials that can be used are, for example, Magnesium or Magnesium alloys, and/or bio-compatible plastic materials that can be used may be, for example, Polyether ether ketone (PEEK) or Poly-L-lactide acid (PLLA). The various parts can be made of the same or of different materials from one another.

A preferred method of manufacturing the receiving part, and optionally also the locking member and/or the bone anchoring element, is an additive manufacturing method, more preferably an additive layer manufacturing method, such as three-dimensional printing. More particularly, preferred methods are laser sintering or laser melting or electron beam melting. In such a method, subsequent layers of a powder material, such as a metal powder, are solidified with an energy beam, particularly a laser or an electron beam, at positions corresponding to the cross-section of the part in the respective layer.

In use, the coupling device 10 may be pre-assembled. For assembly, the locking member 6 may be mounted to the receiving part 5 from the first end 5a or from the second end 5b. In an insertion position of the locking member 6, where the second end 6b of the locking member 6 may be at an axial position above or otherwise near the end portions 58a of the slits 58 of the head receiving portion 52 (see FIG. 15), the accommodation space 54 of the receiving part 5 can expand in the radial direction when the head 3, 3' of the bone anchor is inserted. The pre-assembled coupling device 10 can be connected to a bone anchor 1, 1' either prior to inserting the bone anchor into bone or after the bone anchor has been inserted into bone. In both cases, the head of the bone anchor is inserted into the receiving part 5 through the lower opening 54a and further moved into the accommodation space 54 of the receiving part 5. Due to the slits 58 of the head receiving portion 52, the receiving part 5 snaps onto the head. Thereafter, the locking member 6 is moved downward in the direction of the central axis C to compress the head receiving portion 52 by means of the cooperating tapered inner surface portion 62 of the locking member 6 and the tapered outer surface portion 50c of the receiving part 5. In this position, the inner surface 61 of the locking member 6 is positioned around the head receiving portion 52 and fully or substantially fully encloses the head receiving portion 52. The compression of the head receiving portion 52 may lock the angular position of the bone anchor with respect to the receiving part. If the locking member 6 is configured to be mounted to the receiving part 5 from the first end, the receiving part 5 may first be connected to the bone anchor and then the locking member 6 may be mounted thereafter.

The system including the coupling device and the at least two bone anchors including the first bone anchor 1 and the second bone anchor 1' allows a practitioner to selectively combine the coupling device 10 with either the first bone anchor 1 or the second bone anchor 1'. Hence, using the same coupling device 10, either a monoplanar bone anchoring device or a polyaxial bone anchoring device can be generated. Specifically, when the second bone anchor 1' is inserted into the coupling device, the second bone anchor 1' is configured to pivot around the central axis C in multiple planes. The restraining structure in the form of the recesses 150 provided at the receiving part 5 does not limit, i.e., has no influence on, the pivoting motion of the second bone anchor 1'. At the position where the cutaway portions 151 are formed, the second bone anchor 1' is configured to assume an enlarged pivot angle of its shank axis S with respect to the central axis C. For example, without the cutaway portions 151, a maximum pivot angle of the shank axis S with the central axis C may be approximately 32°, and with the cutaway portions 151, an enlarged pivot angle may be approximately 42°. After insertion of the rod 100, the fixation member 7 is screwed between the legs 56 of the receiving part to secure the rod 100 in the receiving part.

When the first bone anchor 1 is inserted into the coupling device 10, the head 3 is oriented with respect to the coupling device in a manner such that the wings 4 can engage the recesses 150 of the receiving part. By means of this, the pivoting motion of the first bone anchor 1 is restricted to a single plane. In the embodiment, due to the position of the restraining structure, the single plane is a plane defined by the central axis C and by the longitudinal axis L of the rod channel. The cutaway portions 151 provide for an enlarged pivot angle of the second bone anchor 1' with respect to the central axis C. After insertion of the rod 100 the fixation member 7 is screwed between the legs 56 of the receiving part to secure the rod 100 in the receiving part. FIG. 3 shows the locking position of the locking member 6, where the fixation member 7 presses the rod 100 onto the first end 6a of the locking member 6 to keep the locking member 6 in its lowermost position. In the locking position, the second end 6b of the locking member 6 is close to the second end 5b of the receiving part 5 and fully or substantially fully encloses the head receiving portion 52.

A pre-locking of an inserted head 3, 3' may be provided when the locking member 6 is in a pre-locking position slightly above the lowermost position, which still allows for pivoting of the head 3, 3' in the head receiving portion 52 but prevents removal of the head 3, 3' from the head receiving portion 52.

Figure 15:
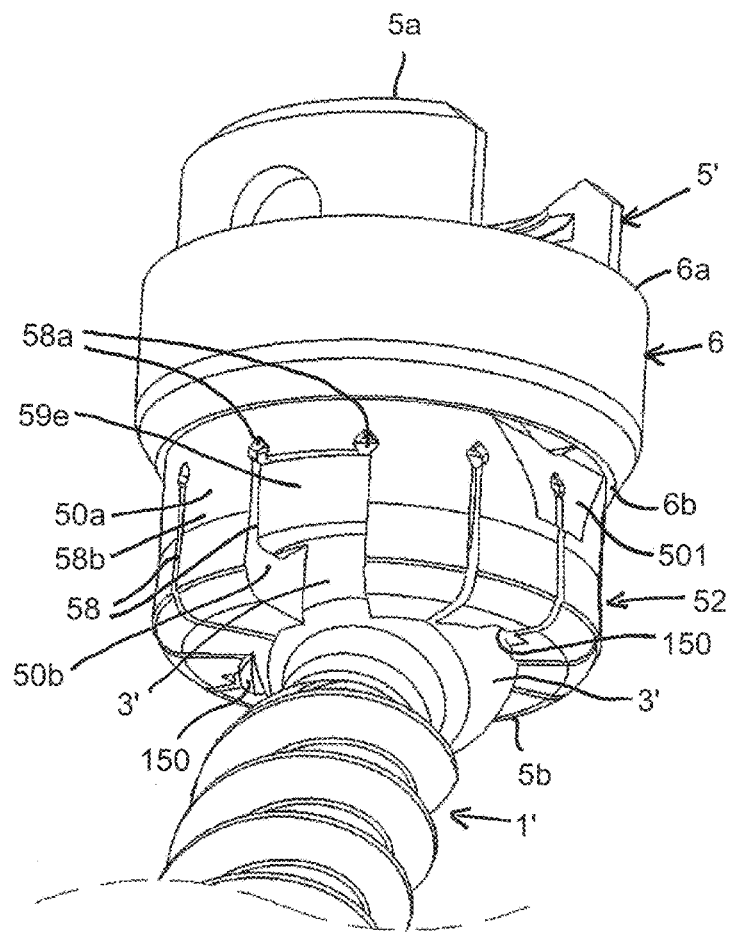
FIG. 15 shows a perspective view of a modified embodiment of the bone anchoring device of FIGS. 1 to 14 in an assembled state.
Figure 18:
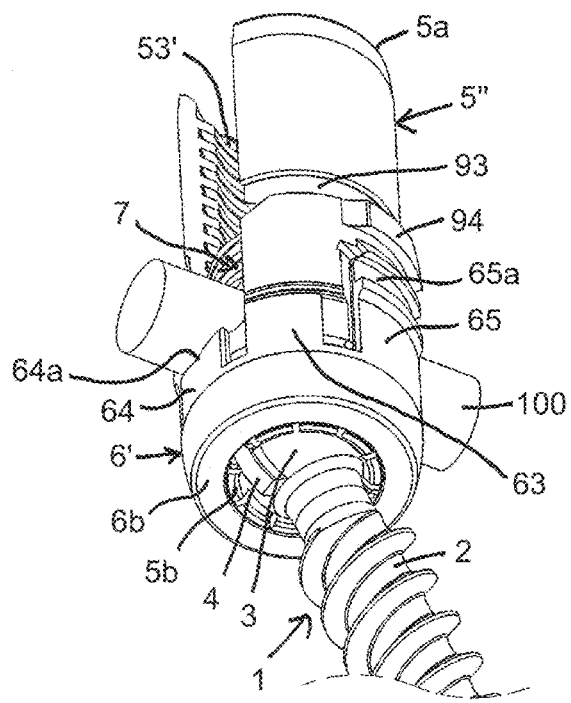
FIG. 18 shows a perspective view from below of the bone anchoring device of FIG. 16 in an assembled state.
Figure 19:
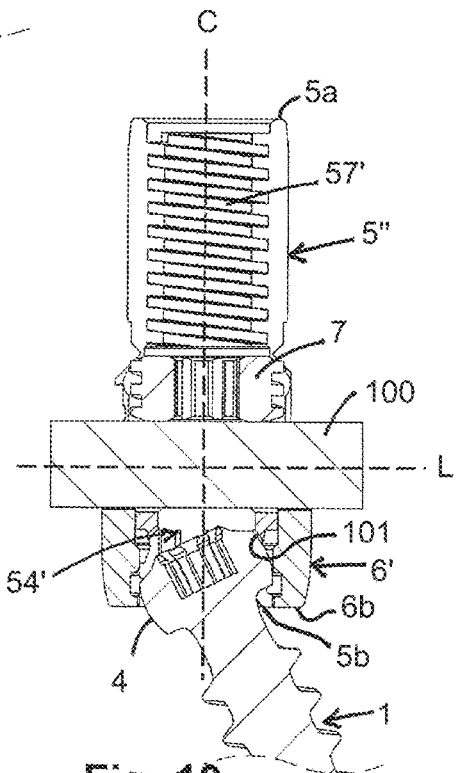
FIG. 19 shows a cross-sectional view of the bone anchoring device of FIGS. 16 and 18, the cross-section taken in a plane including a central axis of the receiving part and a longitudinal axis of an inserted rod.
Figure 20:
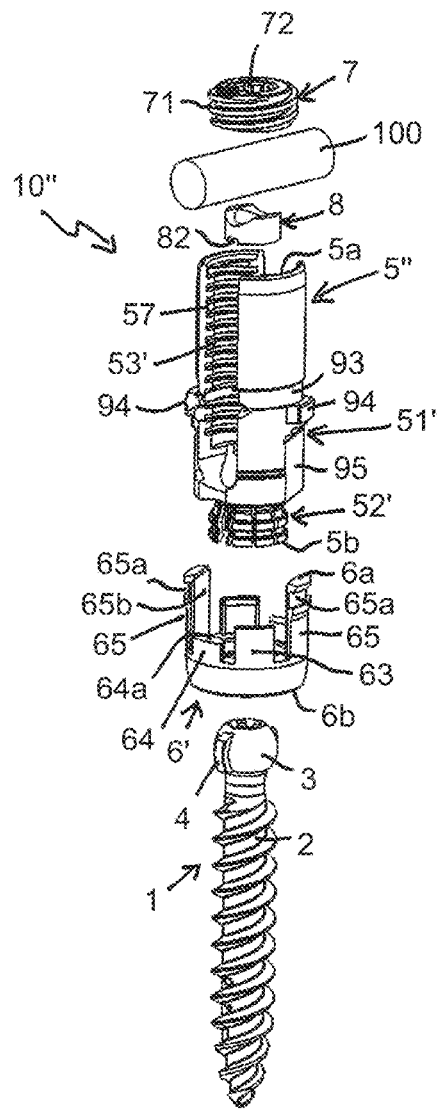
FIG. 20 shows a perspective exploded view of a modified embodiment of the bone anchoring device of FIGS. 16 to 19.
Figure 21:
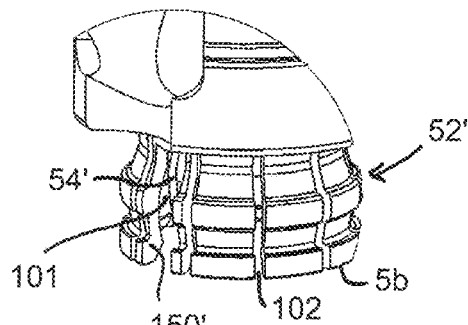
FIG. 21 shows an enlarged perspective view of a lower part of a receiving part of the bone anchoring device of FIG. 20.
Figure 22:
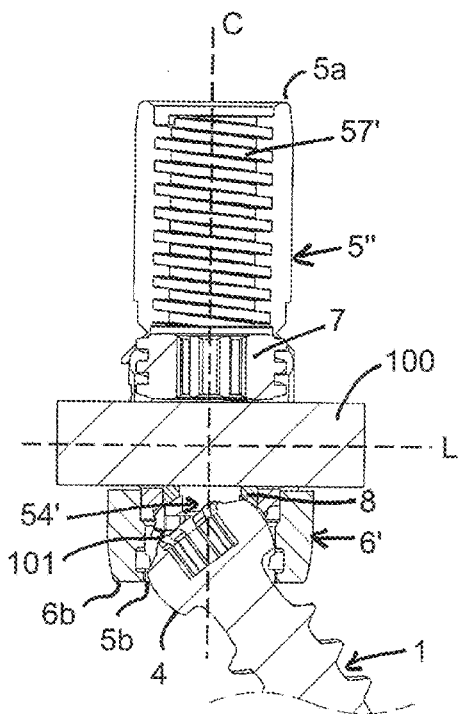
FIG. 22 shows a cross-sectional view of the bone anchoring device of FIG. 20 in an assembled state, the cross-section taken in a plane including a central axis of the receiving part and a longitudinal axis of an inserted rod.
Figure 23:
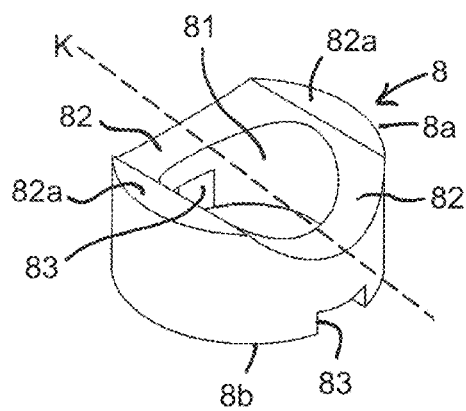
FIG. 23 shows a perspective view from a top of a pressure member of the bone anchoring device of FIGS. 20 and 22.
Figure 24:
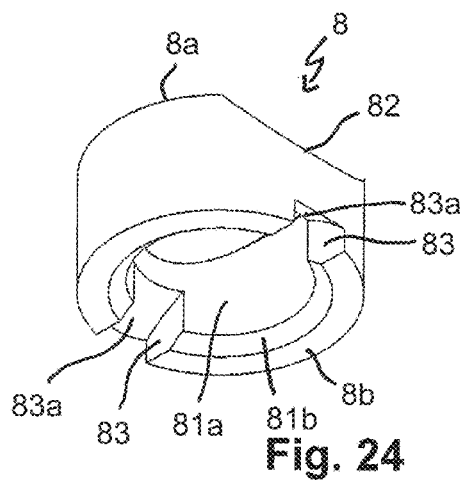
FIG. 24 shows a perspective view from a bottom of the pressure member of FIG. 23.
Figure 25:
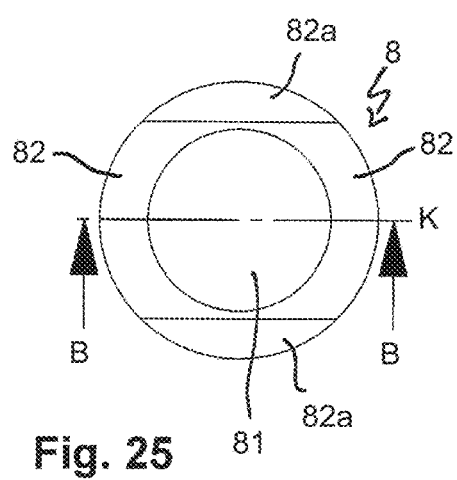
FIG. 25 shows a top view of the pressure member of FIGS. 23 and 24.
Figure 26:
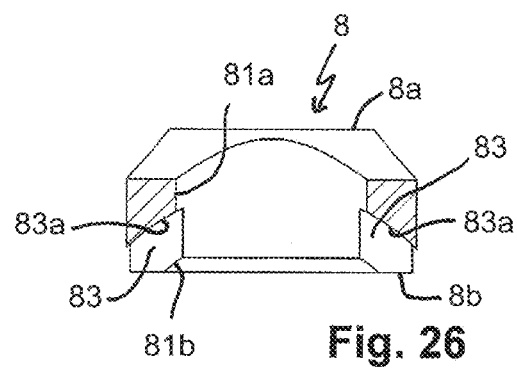
FIG. 26 shows a cross-sectional view of the pressure member of FIGS. 23 to 25, the cross-section taken along line B-B in FIG. 25.

FIG. 15 shows a modification of the coupling device of the embodiment described above with reference to FIGS. 1 to 14. In FIG. 15, similar or identical elements to those of FIGS. 1 to 14 are denoted with the same or similar reference numbers, and descriptions thereof will not be repeated.

The receiving part 5' of the coupling device of FIG. 15 differs from the receiving part 5 of the embodiment of FIGS. 1 to 14 in the configuration of the structure that provides for an enlarged pivot angle. Specifically, instead of or in addition to the cutaway portions 151, for the modified receiving part 5', one of the wall sections 58b of the head receiving portion 52 is at least partially removed, as shown in FIG. 15. The wall section 58b may be partially removed by breaking the selected wall section 58b away at the virtual connection line between the two end portions 58a of the slits 58 delimiting the flexible wall portion 58b, so that only the interior wall portion 59e located above the opening 59a remains. The gap formed by removing a portion of the wall section 58b may be provided at a circumferential position of the receiving part 5' that is different from the circumferential positions of the two recesses 150. The gap provides for a cutout portion configured to receive a portion of the shank of the bone anchor therein to thus provide for an enlarged pivot angle that the shank axis S of the bone anchor can form with the central axis C. The lowermost wall portion 50b and the radially thinner wall portion 50a of the adjacent wall sections 58b, as well as the head 3' of an inserted bone anchor are visible through the gap formed by removing a portion of the wall section 58b. It shall be noted that the position or positions of the enlarged pivot angle can be selected by breaking-off a suitable one or more of the wall sections 58b.

FIG. 15 depicts the coupling device including the modified receiving part 5' with the second bone anchor 1' inserted. However, the modified receiving part 5' can also be connected to the first bone anchor 1. Moreover, in FIG. 15, the locking member 6 is depicted in the insertion position where the second end 6b of the locking member 6 may be at an axial position above the end portions 58a of the slits 58 of the head receiving portion 52, and without a rod being inserted.

The receiving part 5, 5' can be provided with both the cutaway portions 151 and the gap formed by partial removal of one or more of the wall sections 58b, which both provide for an enlarged pivot angle of an inserted shank with respect to the central axis C, or with only one of the cutaway portions 151 or partially removed wall section 58b. The receiving part may also have more than one cutaway portion 151 and/or more than one partially removed wall section 58b. However, the receiving part may also be provided without the cutaway portions 151 or any partially removed wall sections 58b, i.e., without any structure that provides for an enlarged pivot angle. It should be noted here that "an enlarged pivot angle" does not necessarily imply a single enlarged pivot angle that the shank can assume with respect to the central axis C. Rather, the term "enlarged pivot angle" may also refer to a limited circumferential section of the receiving part where the shank can assume a larger pivot angle with respect to the central axis C than at other circumferential sections of the receiving part.

Next, an embodiment of a polyaxial bone anchoring device including a coupling device 10' of a further embodiment and the first bone anchor 1 will be described with reference to FIGS. 16 to 19. The coupling device 10' includes a receiving part 5" for receiving the head 3 of the bone anchor 1 and connecting the bone anchor 1 to a rod 100, and a locking member 6' for locking the head 3 in the receiving part 5". Preferably, the receiving part 5" is a monolithic piece. The coupling device 10' further includes a fixation member in the form of, for example, a fixation screw 7 for securing and fixing the rod 100 in the receiving part 5". The fixation member 7 and the bone anchor 1 may be similar to the fixation member 7 and the first bone anchor 1 of the system described above with reference to FIGS. 1 to 15.

The receiving part 5" has a first or upper end 5a and a second or lower end 5b. Adjacent to the first end 5a, a rod receiving portion 51' is provided, and adjacent to the second end 5b a head receiving portion 52' is provided. The rod receiving portion 51' is substantially cylindrical and has a passage or coaxial bore 53' that extends from the upper end 5a into the head receiving portion 52', and defines a longitudinal central axis C extending through the first end 5a and the second end 5b. The passage 53' includes an internal thread 57' in at least a region thereof for receiving the fixation member 7. A substantially U-shaped recess 55' that forms a channel with a longitudinal axis L for receiving the rod 100 extends from the first end 5a of the receiving part 5" to almost the beginning of the head receiving portion 52'. At a distance from the upper end 5a, a groove or otherwise weakened section 93 may be provided that allows breaking off of the upper portions of the receiving part 5" formed by the U-shaped recess that serve as extended tabs. By means of the extended tabs, it is possible to manipulate the polyaxial bone anchoring device with an inserted rod 100 that is at a higher position compared to the final position so that, for example, a vertebra can be pulled against the rod.

At an outer surface of the rod receiving portion 51' an engagement structure for engagement with an instrument (not shown the figures) may be provided. The engagement structure may include circumferentially extending ribs 94. At a position below the ribs 94, flat outer surface portions 95 are provided at the rod receiving portion 51' that may serve to facilitate assembling of the locking member 6' and/or prevent a rotational movement of the locking member 6' around the central axis C.

As shown in more detail in FIG. 17, the head receiving portion 52' that is formed adjacent the second end 5b of the receiving part 5" has a substantially cap-like shape with a hollow substantially spherical interior portion 101 that defines an accommodation space 54' for pivotably receiving the head 3 therein. A plurality of axially extending slits 102 that are open to the second end 5b and that may extend up to a distance from the second end 5b render the head receiving portion flexible, so that when pressure is exerted onto the head receiving portion by the locking member 6', the head 3 can be clamped and locked.

Two opposite recesses or slots 150' are formed at the bottom end 5*b* of the head receiving portion 52'. The recesses 150' are offset from each other by 180°, and may be aligned with the longitudinal axis L defined by the U-shaped recess 55'. Each recess 150' is open towards the bottom end 5*b* and extends completely through a wall of the head receiving portion 52' in a radial direction, from an inner surface of the wall that delimits the accommodation space 54' to an outer surface of the wall. In the figures, only one of the recesses 150' can be seen, whereas the other one is hidden from view by the head receiving portion 52'. An inner contour of the recesses 150' may be substantially rectangular. The width of the recesses 150' in the circumferential direction of the receiving part 5" may be smaller than the distance between two adjacent slits 102 and may be greater than the width of the slits 102.

By means of the recesses 150', it is possible to insert the head 3 of the first bone anchor 1 from the bottom end 5*b*, with the head 3 oriented in a manner such that the wings 4 can engage the recesses 150' of the receiving part 5". The recesses 150' define a restraining structure or a part of such a restraining structure that restrains a pivoting motion of an inserted head 3 of the bone anchor 1 to a single plane relative to the receiving part including the central axis C. In the present embodiment, due to the position of the restraining structure 150', the single plane is a plane defined by the central axis C and the longitudinal axis L of the rod channel.

The locking member 6' is formed as a closed ring designed to be positioned around and to encompass the head receiving portion 52'. An inner diameter of the locking member 6' is sized such that the locking member 6' fits around the receiving part 5" and is configured to slide along an outer surface of the head receiving portion 52'. The locking member 6' has an internal surface structure that cooperates with the head receiving portion 52' to facilitate the locking of the head 3 in the head receiving portion 52' when the locking member 6' is at its lowermost position or locking position, e.g., when a second or lower end 6*b* of the locking member 6' is close to or adjacent to the second end 5*b* of the receiving part 5". A pre-locking of an inserted head 3 may be provided when the locking member 6' is at a pre-locking position slightly above the lowermost position, which still allows pivoting of the head 3 in the head receiving portion 52' but prevents removal of the head 3 from the head receiving portion 52'.

The locking member 6' of FIGS. 16 to 19 further includes a number of upstanding flexible sections 63 that may serve for engagement with the receiving part 5" to preliminarily hold the locking member 6' in a pre-locking position (not shown in the figures). Also, two opposite projections 64 are provided at an upper side of the locking member 6' that serve for supporting the rod 100 at an upper surface 64*a* provided at the projections 64. In the embodiment shown, the locking member 6' also includes two opposite upstanding arms 65. At an upper end of the arms 65, an engagement structure in the form of grooves 65*a* may be provided that is configured to be engaged by an instrument (not shown in the figures). An inner surface 65*b* of the arms 65 may be flat and configured to cooperate with the flat outer surface portions 95 of the rod receiving portion 51'. The cooperating flat outer surface portions 95 at the receiving part 5" and inner surfaces 65*b* at the locking member 6' may prevent inadvertent rotation of the locking member 6'. In the mounted state, the locking member 6' may assume different axial positions with respect to the receiving part 5", such as an insertion position in which the head 3 of the bone anchor 1 can be inserted, the pre-locking position in which the head is still pivotable with respect to the receiving part 5" but is prevented from removal therefrom, and a locking position in which the head 3 is locked at a particular angular position relative to the receiving part.

The locking member 6' and the receiving part 5" may be pre-assembled by mounting the locking member 6' to the receiving part 5" from the second end 5*b* of the receiving part 5". If a monoplanar bone anchoring device is desired, the first bone anchor 1 is used. The head 3 of the first bone anchor 1 may be inserted into the accommodation space 54' of the receiving part 5" from the second end 5*b* thereof when the locking member 6' is at the insertion position. The wings 4 extend into the recesses 150'. Due to the slits 102, the head receiving portion 52' is flexible and snaps onto the head. Thereafter, the locking member 6' can be moved downward, for example, with an instrument (not shown), whereby the locking member 6' compresses the head receiving portion 52' so that pressure is exerted on the head. If necessary, the locking member 6' may be moved upwards, for example with an instrument, to loosen the locking of the head. The rod 100 may already be inserted into the substantially U-shaped recess 55' and the fixation member 7 may then be screwed into the passage 53' of the receiving part 5". Due to the extended tabs of the receiving part 5", the rod 100 may still be movable so that the head can be locked independently from the rod. For final locking, the fixation member 7 is tightened so that the rod 100 presses onto the surface 64*a* of the locking member 6', which further moves the locking member 6' into the locking position.

In a modification of the receiving part 5" of FIGS. 16 to 19, the receiving part 5" may be provided with the cutaway portions 151 described above with reference to FIGS. 1 to 15, to provide for an enlarged pivot angle of the bone anchor with respect to the central axis C.

The coupling device 10' of the present embodiment may also be coupled to the second bone anchor 1' described above with reference to FIGS. 1 to 15. When the coupling device 10' is assembled with the second bone anchor 1', the resulting bone anchoring device is a polyaxial bone anchoring device, in which the bone anchor can pivot in multiple planes. Thus, the first bone anchor 1 and the second bone anchor 1' may be interchangeably used together with one and the same coupling device 10'. Alternatively or in addition, at least one wall section delimited by two adjacent slits 102 of the head receiving portion 52' may be at least partially removed to provide for an enlarged pivot angle of the bone anchor with respect to the central axis C.

Next, a further modification of the coupling device will be described with respect to FIGS. 20 to 26. In FIGS. 20 to 26, similar or identical elements to those of FIGS. 16 to 19 are denoted with the same or similar reference numbers, and descriptions thereof will not be repeated.

The coupling device 10" of FIGS. 20 to 26 differs from the coupling device 10' of FIGS. 16 to 19 in that a pressure member 8 is provided in addition to the receiving part 5" and the locking member 6'. The pressure member 8 is configured to be arranged within the passage 53' of the receiving part 5" and configured to contact an inserted head 3, 3' from above to additionally exert pressure onto the inserted head. Preferably, the pressure member 8 is configured to exert pressure onto an inserted head only from above.

As can best be seen in FIGS. 23 to 26, the pressure member 8 extends from a first or upper end 8*a* to a second or lower end 8*b*, and has a central passage 81 extending from the first end 8*a* to the second end 8*b*. A first portion 81*a* of the passage 81 adjacent the first end 81*a* is substantially cylindrical and forms a substantially cylindrical inner surface of the pressure member 8. Adjacent to the second end 8b, a second portion 81b of the passage 81 has a substantially spherically-shaped inner surface configured to contact the spherically-shaped outer surface portion of the head 3 from above.

At its first end 8a, the pressure member 8 includes a rod support surface 82 for supporting an inserted rod 100. The rod support surface 82 defines a channel axis K of the pressure member 8. Adjacent the rod support surface 82, opposing flat surfaces 82a may be formed at the first end 8a of the pressure member 8.

At the second end 8b of the pressure member 8, two opposite recesses or slots 83 are formed, which are open to the second end 8b. The recesses 83 are offset from each other by 180°, and are aligned with the axis K defined by the rod support surface 82 in the embodiment shown. An inner contour of the recesses 83 may be substantially rectangular. An upper portion 83a that delimits the recesses 83 towards the first end 8a of the pressure member 8 may have a curved shape that corresponds to a shape of the upper end 4a of the wings 4 provided at the head 3 of the first bone anchor 1.

The recesses 83 are configured to receive a portion of the wings 4 of the head 3 of the first bone anchor 1 therein. Specifically, the recesses 83 of the pressure member 8, together with the recesses 150' provided at the receiving part 5", define a restraining structure or a part of such a restraining structure, that restrains a pivoting or rotational motion of an inserted head of a bone anchor to a single plane including the central axis C.

The pressure member 8 is mounted to the receiving part 5" at an orientation such that the recesses 83 of the pressure member 8 are aligned with the recesses 150' of the receiving part 5" in the circumferential direction, and the axis K defined by the rod support surface 82 is aligned with the longitudinal axis L defined by the U-shaped recess 55' of the receiving part 5".

In use, depending on the selection of the bone anchor, the coupling device 10" can be assembled with the first bone anchor to form a monoplanar bone anchoring device, or with the second bone anchor to form a polyaxial bone anchoring device. The final locking of the head is achieved by exerting pressure with the rod onto the pressure member 8, which in turn locks the head in the head receiving portion.

Further modifications of the above described embodiments are also conceivable. For example, the restraining structure in the receiving part 5, 5', 5" and/or the pressure member 8 can be at another position so that the single pivot plane can be arranged at an angle with respect to the channel axis. It may also be possible to provide multiple restraining structures at different locations such that several distinct pivot planes are provided, one of which can be selected when inserting the first bone anchor. Moreover, a further bone anchor of a third type may be provided that cooperates with the one or more than one restraining structures provided at the receiving part and/or the pressure member in such a way that the bone anchor assumes a predefined angular orientation with respect to the central axis C, and is prevented from pivoting, i.e., where such a further bone anchor and coupling device form a monoaxial bone anchoring device.

The first bone anchor may have wings or any other restraining structure which are spaced apart from the free end of the head in some embodiments.

It shall be noted that particular shapes of the individual parts and elements described above are not limited to the specific shape shown in the drawings but may vary.

The bone anchor is not limited to having a threaded shank. All types of bone anchors that are suitable for anchoring in bone or vertebrae may be used.

In a further modification, the bone anchor can be a two part bone anchor that includes a shank and a separate head connectable to the shank. Thus, different heads can be provided that can selectively be combined with a same shank. For example, one of the heads can be the head 3 including the restraining structure, such as the wings, and another head can be a head 3' with a spherical outer surface as described without a restraining structure. In other words, a monoplanar head or a polyaxial head can selectively be combined with a same shank. Such a design may further increase or enhance the modularity of the system.

Instead of the fixation member described above, other fixation devices may be used, such as, for example, a bayonet fixation device or a two part fixation device that allows for independent fixation of the rod and the head.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A system for coupling a rod to bone, the system comprising:
   a first bone anchor comprising a first shank for anchoring to bone and a first head;
   a second bone anchor different from the first bone anchor and comprising a second shank for anchoring to bone and a second head; and
   a coupling device comprising:
      a receiving part having a first end, an opposite second end, and a central axis extending between the first end and the second end, the receiving part comprising a rod receiving portion at the first end for receiving a rod, and a head receiving portion at the second end that defines an accommodation space for interchangeably accommodating the first head of the first bone anchor or the second head of the second bone anchor; and
      a locking member positionable at least partially around the head receiving portion and movable between at least a first position where a head that is held in the accommodation space is movable relative to the receiving part, and a second position where the head that is held in the accommodation space is locked relative to the receiving part;
   wherein the coupling device comprises a restraining surface configured to cooperate with the first bone anchor to restrict pivoting of the first bone anchor relative to the receiving part, and wherein the coupling device is configured to cooperate with the second bone anchor to restrict pivoting of the second bone anchor relative to the receiving part differently than the restricted pivoting of the first bone anchor relative to the receiving part.

2. The system of claim 1, wherein when either the first bone anchor or the second bone anchor is connected to the receiving part, the connected bone anchor is configured to assume a plurality of angular positions relative to the receiving part.

3. The system of claim 1, wherein when the first bone anchor is connected to the receiving part, the restraining surface restricts pivoting of the first bone anchor relative to the receiving part within a single plane that includes the central axis.

4. The system of claim 3, wherein when the second bone anchor is connected to the receiving part, the second bone anchor is pivotable in multiple different planes relative to the receiving part.

5. The system of claim 1, wherein when the first bone anchor is connected to the receiving part, the restraining surface forms a monoaxial connection where the first bone anchor is prevented from pivoting away from the central axis of the receiving part in every radial direction.

6. The system of claim 1, wherein the restraining surface defines at least one recess in the head receiving portion that is configured to cooperate with a corresponding restraining structure of the first bone anchor to restrict the pivoting of the first bone anchor.

7. The system of claim 6, wherein the at least one recess extends from an inner surface of the head receiving portion that defines the accommodation space towards an outer surface of the head receiving portion.

8. The system of claim 6, wherein the at least one recess comprises two recesses that are offset from one another by 180°.

9. The system of claim 6, wherein the accommodation space has a spherical segment-shaped portion including a greatest inner width of the sphere measured in a direction perpendicular to the central axis, and wherein the at least one recess extends axially through a portion of the accommodation space with the greatest inner width of the sphere.

10. The system of claim 1, wherein the head receiving portion further comprises a cutout portion at the second end of the receiving part configured to facilitate angulation of a connected bone anchor at an enlarged pivot angle relative to the receiving part in at least one direction with respect to the central axis.

11. The system of claim 10, wherein the cutout portion is substantially aligned with the restraining surface in a circumferential direction around the central axis.

12. The system of claim 1, wherein the head receiving portion defines a plurality of slits that extend from the second end of the receiving part towards the first end of the receiving part, the slits forming a plurality of wall sections that render the head receiving portion compressible and/or expandable.

13. The system of claim 12, wherein at least one of the plurality of wall sections is configured to be separated from the rest of the receiving part to form a cutout portion of the receiving part configured to facilitate angulation of a connected bone anchor at an enlarged pivot angle relative to the receiving part in at least one direction with respect to the central axis.

14. The system of claim 1, wherein a wall of the head receiving portion comprises at least one cavity configured to reduce a thickness of the wall in a radial direction between the accommodation space and an outer surface of the head receiving portion.

15. The system of claim 1, wherein an outer surface of the head receiving portion and an inner surface of the locking member are configured to cooperate in a manner such that adjusting the locking member from the first position to the second position increases a compression force of the locking member on the head receiving portion to clamp an inserted head in the receiving part.

16. The system of claim 1, further comprising a pressure member positionable in the receiving part to exert pressure on an inserted head to clamp the head at a particular angular position relative to the receiving part.

17. The system of claim 1, wherein the head of the first bone anchor has a substantially spherically-shaped outer surface portion and further comprises a restraining surface formed by a projection at the outer surface portion that is configured to cooperate with the restraining surface of the coupling device.

18. A method for coupling a rod to a bone using a system comprising a first bone anchor comprising a first shank for anchoring to bone and a first head, a second bone anchor different from the first bone anchor and comprising a second shank for anchoring to bone and a second head, and a coupling device comprising a receiving part having a first end, an opposite second end, and a central axis extending between the first end and the second end, the receiving part comprising a rod receiving portion at the first end for receiving a rod, and a head receiving portion at the second end that defines an accommodation space for interchangeably accommodating the first head of the first bone anchor or the second head of the second bone anchor, and a locking member positionable at least partially around the head receiving portion, the method comprising:
    selecting the first bone anchor or the second bone anchor and assembling the selected bone anchor to the coupling device when the locking member is at a first position;
    moving the receiving part relative to the head of the selected bone anchor that is held in the accommodation space to a desired position when the locking member is at the first position, wherein the coupling device comprises a restraining surface configured to cooperate with the first bone anchor to restrict pivoting of the first bone anchor relative to the receiving part, and wherein the coupling device is configured to cooperate with the second bone anchor to restrict pivoting of the second bone anchor relative to the receiving part differently than the restricted pivoting of the first bone anchor relative to the receiving part; and
    adjusting the locking member from the first position to a second position, such that the head of the selected bone anchor that is held in the accommodation space is locked relative to the receiving part.

19. The method of claim 18, further comprising implanting the selected bone anchor in bone before the selected bone anchor is assembled to the coupling device.

20. A system for coupling a rod to bone, the system comprising:
    a first bone anchor comprising a first shank for anchoring to bone and a first head;
    a second bone anchor different from the first bone anchor and comprising a second shank for anchoring to bone and a second head; and
    a coupling device comprising:
        a receiving part having a first end, an opposite second end, and a central axis extending between the first end and the second end, the receiving part comprising a rod receiving portion at the first end for receiving a rod, and a head receiving portion at the second end that defines an accommodation space for interchangeably accommodating the first head of the first bone anchor or the second head of the second bone anchor; and
        a locking member positionable at least partially around the head receiving portion and movable between at least a first position where a head that is held in the accommodation space is movable relative to the receiving part, and a second position where the head that is held in the accommodation space is locked relative to the receiving part;

wherein the coupling device comprises a restraining surface configured to cooperate with the first bone anchor to restrict pivoting of the first bone anchor relative to the receiving part to a single plane that includes the central axis, and wherein the coupling device is configured to cooperate with the second bone anchor to restrict pivoting of the second bone anchor relative to the receiving part differently than the restricted pivoting of the first bone anchor relative to the receiving part.

* * * * *